United States Patent
Forohar et al.

(10) Patent No.: US 11,440,873 B1
(45) Date of Patent: Sep. 13, 2022

(54) METHOD OF ELECTROCHEMICAL SUBSTITUTION OF AZIDES FOR HYDROGEN ON TERTIARY CARBONS

(71) Applicant: The United States of America as Represented by the Secretary of the Navy, Indian Head, MD (US)

(72) Inventors: Farhad Forohar, LaPlata, MD (US); Victor Bellitto, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 157 days.

(21) Appl. No.: 16/873,402

(22) Filed: Apr. 7, 2020

(51) Int. Cl.
  *B01J 19/08* (2006.01)
  *C07C 247/14* (2006.01)
  (Continued)

(52) U.S. Cl.
  CPC ........... *C07C 247/14* (2013.01); *B01J 19/088* (2013.01); *C25B 3/00* (2013.01); *C25B 11/057* (2021.01);
  (Continued)

(58) Field of Classification Search
  CPC ... C07C 247/14; C07C 247/16; C07C 51/353; C07C 2101/14; C07C 51/347; C07C 51/377; C25B 11/057; C25B 3/00; C25B 15/02; C25B 3/02; C25B 3/23; C25B 9/08; C25B 11/0478; C25B 11/0405; C25B 11/0415; B01J 19/088; B01J 2219/0809; B01J 2219/0839; B01J 2219/0841; B01J 2219/0877; C08J 5/06; C22C 49/14; D01F 11/127; D06M 11/83; C12P 19/34; C12P 7/44; G01N 33/547; C12N 9/96;
  (Continued)

(56) References Cited

U.S. PATENT DOCUMENTS 4,050,997 A * 9/1977 Heissler ..................... C08J 5/06
                                                      205/138
7,488,859 B2   2/2009 Huang et al.
  (Continued)

FOREIGN PATENT DOCUMENTS

RU    2551683 C1    5/2015

OTHER PUBLICATIONS httpsi//doi.org/ 1 0.1 021 /jo00443a024—Publicalion Date: Nov. 1, 1977—Synthesis of adamantane derivatives.3T. A convenient and efficient synthesis of 1-azidoadamantane and related bridgehead azides, and some of their reactions—Tadashi Sasaki, Shoji Eguchi, Tomonori Katada and Osamu HilRoaki.

*Primary Examiner* — Xiuyu Tai
(74) *Attorney, Agent, or Firm* — Fredric J. Zimmerman

(57) ABSTRACT

A method of substituting an azide for hydrogen bonded to a tertiary carbon atom is provided. A liquid mixture in an oxygen-free environment has spaced-apart carbon and platinum electrodes disposed therein. The liquid mixture includes a solvent, ammonium azide, and a base material having at least one tertiary carbon atom with hydrogen bonded thereto. An electric current is applied to the electrodes where the liquid mixture undergoes a reaction. The electrochemically-induced reaction yields a liquid product and a solid product. The liquid product includes the solvent and a constituent having at least one tertiary carbon atom with an azide bonded thereto.

19 Claims, 1 Drawing Sheet

(51) Int. Cl.
 *C25B 15/02* (2021.01)
 *C25B 3/00* (2021.01)
 *C25B 11/057* (2021.01)

(52) U.S. Cl.
 CPC ....... *C25B 15/02* (2013.01); *B01J 2219/0809* (2013.01); *B01J 2219/0839* (2013.01); *B01J 2219/0841* (2013.01); *B01J 2219/0877* (2013.01)

(58) Field of Classification Search
 CPC .................. C12N 9/1264; C07H 9/10; C12Y 207/07031; C01B 21/08; C01B 32/50; C01P 2002/70; C01P 2002/82; B82Y 40/00; C08G 63/78; C07B 2200/09
 See application file for complete search history.

(56) References Cited

U.S. PATENT DOCUMENTS

| | | |
|---|---|---|
| 8,188,326 B2 | 5/2012 | Kawai |
| 8,367,166 B2 | 2/2013 | Dahl et al. |
| 2017/0362084 A1 | 12/2017 | Nakata et al. |
| 2019/0368057 A1 | 12/2019 | Lin et al. |
| 2021/0238577 A1* | 8/2021 | Nguyen ................. C12P 19/34 |

* cited by examiner

METHOD OF ELECTROCHEMICAL SUBSTITUTION OF AZIDES FOR HYDROGEN ON TERTIARY CARBONS

ORIGIN OF THE INVENTION

The invention described herein was made in the performance of official duties by employees of the Department of the Navy and may be manufactured, used, licensed by or for the Government for any governmental purpose without payment of any royalties thereon.

FIELD OF THE INVENTION

The invention relates generally to azidation of tertiary carbons, and more particularly to an electrochemical method of substituting azides for hydrogen on tertiary carbon molecules.

BACKGROUND OF THE INVENTION

An azide is any of a class of compounds that contains three nitrogen (N) atoms as a group. In general, azides are represented as "—$N_3$". Azides are versatile functional groups that can be used to add energetic power to molecules.

SUMMARY OF THE INVENTION

Accordingly, it is an object of the present invention to provide a method of making an energetic material that includes azides.

Another object of the present invention is to provide a simple and cost efficient method of making materials more energetic by replacing an element thereof with an azide.

Other objects and advantages of the present invention will become more obvious hereinafter in the specification and drawings.

In accordance with the present invention, a method of substituting an azide for hydrogen bonded to a tertiary carbon atom is provided. A liquid mixture is provided in an oxygen-free environment. A carbon electrode and a platinum electrode are disposed in the liquid mixture in a spaced-apart fashion. The liquid mixture includes a solvent, a soluble azidation reagent (e.g., ammonium azide), and a base material having at least one tertiary carbon atom with hydrogen bonded thereto. An electric current is applied to the carbon electrode and platinum electrode wherein the liquid mixture undergoes a reaction. The electrochemically-induced reaction yields a liquid product and a solid product. The liquid product includes the solvent and a constituent having at least one tertiary carbon atom with an azide bonded thereto.

BRIEF DESCRIPTION OF THE DRAWINGS

Other objects, features and advantages of the present invention will become apparent upon reference to the following description of the exemplary embodiments and to the drawings, wherein corresponding reference characters indicate corresponding parts throughout the several views of the drawings and wherein.

DETAILED DESCRIPTION OF THE INVENTION

Figure 1:
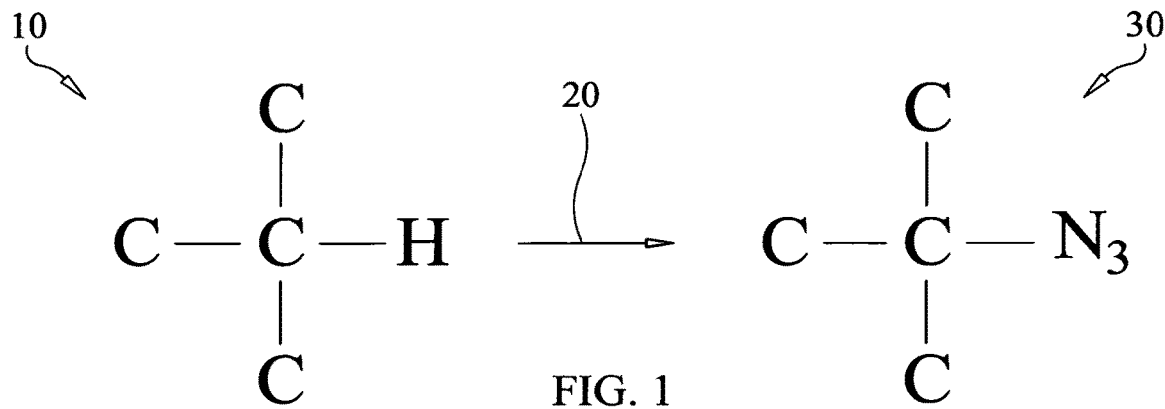
FIG. 1 is a schematic depiction of the electrochemical substitution of an azide for hydrogen bonded to a tertiary carbon atom in accordance with an embodiment of the present invention.

Referring now to the drawings and more particularly to FIG. 1, a schematic of an electrochemical process in accordance with an embodiment of the present invention is illustrated. A molecule 10 having hydrogen (H) bonded to a tertiary carbon (C) atom thereof undergoes an electrochemically-induced reaction 20 to yield a molecule 30 having an azide ($N_3$) substituted for the hydrogen bonded to molecule 10. The resulting molecule 30 is more energetic than molecule 10.

Molecule 10 is part of a base material that is to be processed electrochemically in accordance with the present invention. It is to be understood that the base material could have one or more tertiary carbon sites without departing from the scope of the present invention. By way of an illustrative example, the present invention will be explained with respect to single azide substitution. However, it is to be understood that the basic electrochemical method to be described herein could also be used for the substitution of multiple azides in the case of base materials having multiple tertiary carbon sites to thereby yield di, tri, and even tetra azide compounds.

Figure 2:
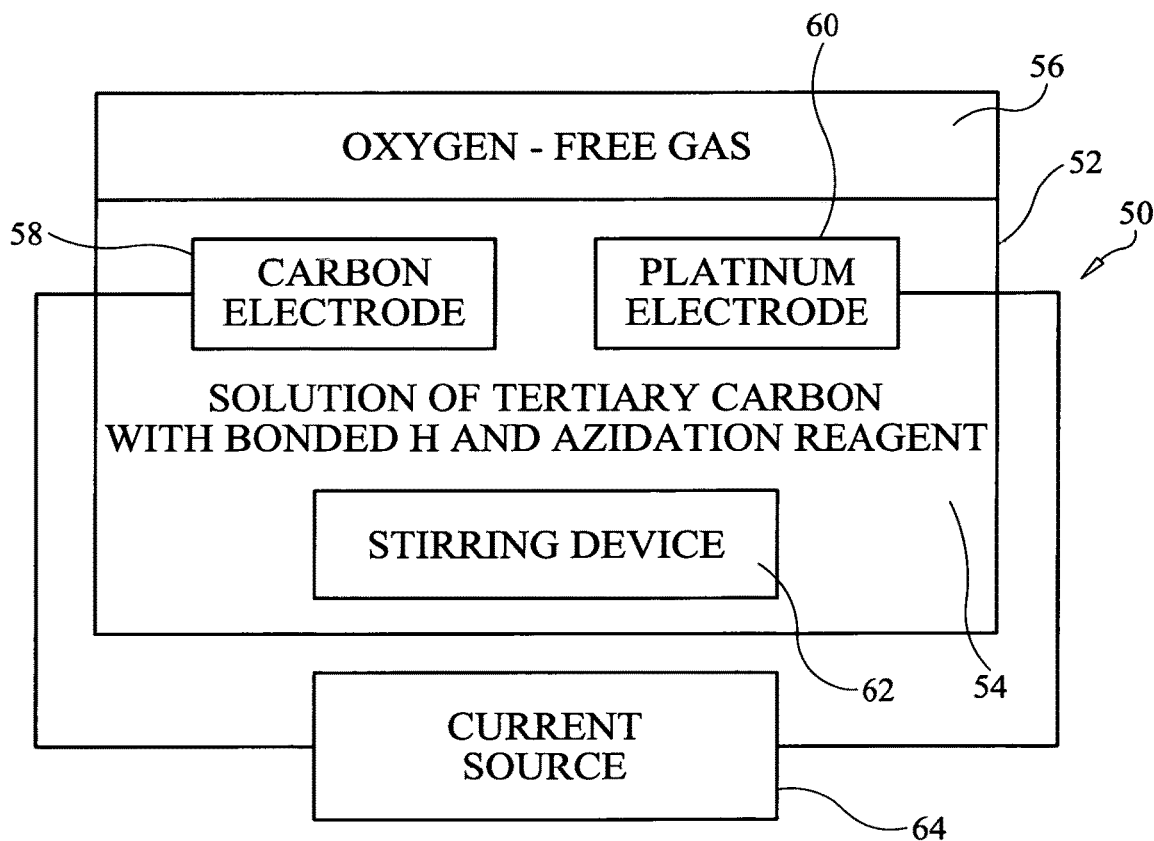
FIG. 2 is a schematic view of an apparatus used to substitute an azide for hydrogen bonded to tertiary carbon atom in accordance with embodiment of the present invention.

The electrochemical process of the present invention will now be explained with reference to FIG. 2 where an apparatus for carrying out the process is referenced generally by numeral 50. A sealed or sealable container 52 is partially filled with a liquid mixture 54. The remaining portion of container 52 is filled with an oxygen-free gas 56 such as argon, nitrogen, etc. Disposed in liquid mixture 54 are two spaced-apart electrodes. More specifically, apparatus 50 employs a carbon electrode 58 and a platinum electrode 60. The sizes and shapes of the electrodes may be used to control the speed of the electrochemical reaction that will occur in liquid mixture 54. Accordingly, it is to be understood that the sizes and shapes of electrodes 58 and 60 may be varied without departing from the scope of the present invention.

Apparatus 50 can also include a stirring device 62 disposed in liquid mixture 54. Stirring device 62 can be any type of agitating or rotating device that keeps liquid mixture 54 moving during the electromechanical reaction process. An electric current source 64 is connected to electrodes 58 and 60. Current source 64 applies an electric current to electrodes 58 and 60 to initiate and maintain an electrochemical reaction within liquid mixture 54. After a period of time, liquid mixture 54 separates into a liquid product and a solid product. As will be explained and supported by an example of the present invention presented herein, the material constituent of interest having at least one tertiary carbon atom with an azide bonded thereto is contained within the liquid product resulting from the electrochemical reaction.

Liquid mixture 54 is a solution that includes solvent, a base material that has at least one tertiary carbon atom with hydrogen bonded thereto, and a soluble azidation reagent that provides the azide(s) that will be substituted for the carbon-bonded-hydrogen in the base material. A suitable azidation reagent is ammonium azide owing to its ability to achieve complete dissolution in liquid mixture 54 to thereby prevent fouling of electrodes 58 and 60. A suitable base material for use in the present invention is adamantane which has four tertiary carbons in its structure. Adamantane is commercially available and inexpensive. The solvent in liquid mixture 54 can be anhydrous acetonitrile with a lithium percholate electrolyte mixed therein. Additional components of liquid mixture 54 can include a proton such as acetic acid and a catalyst such as manganese (II) bromide tetrahydrate.

Actual Example

By way of an illustrative, actual example, liquid mixture 54 was formulated as follows:
- a base material of 250 milligrams of adamantane;
- solvent of 90 milliliters of 0.1 mole lithium percholate dissolved in anhydrous acetonitrile;
- an azidation reagent of 2.7 grams of ammonium azide;
- a proton source of 10 milliliters of acetic acid; and
- a catalyst of 100 milligrams of manganese (II) bromide tetrahydrate.

The above-formulated liquid mixture was used to partially fill a container (e.g., container 52). The container was then sealed to define a gaseous volume in the container along with the liquid mixture. The gaseous volume was then filled with an oxygen-free gas (e.g., a gas 56 such as argon) that is maintained throughout the present invention's reaction process. The liquid mixture was stirred (e.g., using stirring device 62) at room temperature and an electric current was applied thereto via the above-described electrodes 58 and 60 powered by current source 64. For the instant example, a constant electric current of 40 milliamps was applied to the electrodes and maintained for 8 hours. During the application of the electric current, the liquid mixture separated into a solid product and a liquid product. As noted above, the liquid product contains the constituent material of interest having at least one carbon atom whose hydrogen has been replaced by an azide.

To verify the efficacy of the above-described process, the reaction's generated liquid product was further processed to yield a solid that could be examined by mass spectroscopy. As a first step, the solvent is removed from the liquid product. For the illustrated example, the liquid product underwent rotary evaporation at the elevated temperature of 40° C. to yield a paste. This solvent-evaporated paste was mixed with ethyl ether and stirred for several hours at room temperature whereby an ethereal solution and solid were formed. The ethereal solution was processed to remove the ethyl ether. More specifically, the ethereal solution was mixed with 5% sodium bicarbonate and water to a neutral pH. The pH-neutralized ethereal solution was then dried to evaporate out the ethyl ether. In the example, the pH-neutralized ethereal solution was dried over sodium sulfate and concentrated by rotary evaporation to yield 80 milligrams of a solid that was identified as mono or 1-azidoadamtane.

As mentioned above, the present invention may be used to electrochemically substitute an azide atom for one or more of a base material's hydrogen-bonded tertiary carbons. In the illustrated example, the base material of adamantane has four tertiary carbons with hydrogen bonded thereto. While the above post-processing of the electrochemical reaction's liquid product yielded a 1-azidoadamantane solid, the present invention may be used to generate multi-azido-adamantanes as will be explained immediately below.

The melting point of unsubstituted adamantane is 270° C. Adding one azide lowers the melting point to 81° C. and adding two azides lowers the melting point further to 27° C. Thus, it is possible that if 3 or 4 azides are added to the adamantane, the products become volatile at ambient conditions. This reasoning may explain both the yield of the solid 1-azidoadamantane in the above example as well as the absence of multi-azidoadamantanes. That is, during the rotary evaporation processing at 40° C. used to remove the solvent as described above, it was hypothesized that the elevated processing temperature may have inadvertently removed the multi-azidoadamantanes. Therefore, during subsequent example runs using the same starting liquid mixture, the products were trapped at different temperatures and evaluated. For example and in one experimental run, after the electrochemical reaction was completed, about 5 milliliters of the liquid product was distilled using trap-by-trap vacuum distillation. Products were collected at temperatures of −25° C., −56° C., and −75° C. The content of the −75° C. trap had a mass spectrum that indicated the presence of tri-azidoadamantane. More specifically, the molecular weight of tri-azidoadamantane is 259.12. If one $N_3$ is detached, the molecular weight becomes 231.12. For the product trapped at −75° C., the mass spectrum of the sample had molecular weights of 259.19 and 231.16 thereby approximating the values expected for tri-azidoadamantane. Accordingly, the process described herein yields a liquid product that includes at least one tertiary carbon atom with an azide bonded thereto where the subsequent liquid product processing can be tailored to yield the desired azidoadamantane(s).

The exemplary azidation reagent of ammonium azide is a better azidation reagent than metal azides such as sodium azide. When sodium azide was used in the above-described process, a suspension (i.e., not a clear solution) formed causing the electrodes to become covered with a solid layer shortly after the electric current was applied to the electrodes. At that point, the current dropped to zero, the reaction stopped, and the electrodes had to be removed/cleaned/reinserted only to work for a short time before fouling occurred again. In contrast, this problem was not observed when ammonium azide was used. Ammonium azide easily dissolved in the reaction medium and formed a clear colorless liquid (i.e., no suspension). Additionally, the electrochemical reaction proceeded with no interruption of current flow.

The advantages of the present invention are numerous. The electrochemical process described herein is a simple approach to producing energetic azide materials from less energetic tertiary carbon materials. Electric current levels and the duration of the application of the current are easily adjusted to tailor the ultimate output product.

Although the invention has been described relative to specific exemplary embodiments thereof, there are numerous variations and modifications that will be readily apparent to those skilled in the art in light of the above teachings. It is therefore to be understood that, within the scope of the appended claims, the invention may be practiced other than as specifically described.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should be at least construed in light of the number of significant digits and by applying ordinary rounding.

What is claimed is:

1. A method of substituting an azide for hydrogen bonded to at least one tertiary carbon atom, comprising:
   providing a liquid mixture in an oxygen-free environment with a carbon electrode and a platinum electrode disposed in said liquid mixture in a spaced-apart fashion, said liquid mixture includes a solvent, ammonium azide, and a base material having said at least one tertiary carbon atom with the hydrogen bonded thereto; and
   applying an electric current to said carbon electrode and said platinum electrode wherein said liquid mixture undergoes a reaction to yield a liquid product and a solid product, said liquid product includes said solvent and a constituent having said at least one tertiary carbon atom with an azide bonded thereto.

2. The method according to claim 1, wherein said base material comprises adamantane.

3. The method according to claim 1, further comprising stirring said liquid mixture at room temperature during said step of applying.

4. The method according to claim 1, wherein said base material comprises adamantane, wherein said solvent comprises lithium percholate dissolved in anhydrous acetonitrile, and wherein said liquid mixture further includes acetic acid and a catalytic quantity of manganese (II) bromide tetrahydrate.

5. The method according to claim 1, wherein said base material comprises 250 milligrams of adamantane, wherein said solvent comprises 90 milliliters of 0.1 mole of lithium percholate dissolved in anhydrous acetonitrile, wherein said liquid mixture includes 2.7 grams of said ammonium azide, and wherein said liquid mixture further includes 10 milliliters of acetic acid and 100 milligrams of manganese (II) bromide tetrahydrate.

6. The method according to claim 5, further comprising stirring said liquid mixture at room temperature during said step of applying.

7. The method according to claim 1, further comprising removing said solvent from said liquid product wherein a paste is generated;
   mixing ethyl ether with said paste wherein an ethereal solution is generated that includes said constituent; and
   evaporating said ethyl ether from said ethereal solution to yield said constituent in a solid state.

8. A method of substituting an azide for hydrogen bonded to at least one tertiary carbon atom, comprising:
   providing a liquid mixture that includes a solvent, ammonium azide, and a base material having said at least one tertiary carbon atom with the hydrogen bonded thereto;
   disposing said liquid mixture in an oxygen-free environment;
   positioning a carbon electrode and a platinum electrode in a spaced-apart fashion in said liquid mixture; and
   applying an electric current to said carbon electrode and said platinum electrode wherein said liquid mixture undergoes a reaction to yield a liquid product and a solid product, said liquid product includes said solvent and a constituent having said at least one tertiary carbon atom with an azide bonded thereto.

9. The method according to claim 8, wherein said base material comprises adamantane.

10. The method according to claim 8, further comprising stirring said liquid mixture at room temperature during said step of applying.

11. The method according to claim 8, wherein said base material comprises adamantane, wherein said solvent comprises lithium percholate dissolved in anhydrous acetonitrile, and wherein said liquid mixture further includes acetic acid and a catalytic quantity of manganese (II) bromide tetrahydrate.

12. The method according to claim 8, wherein said base material comprises 250 milligrams of adamantane, wherein said solvent comprises 90 milliliters of 0.1 mole of lithium percholate dissolved in anhydrous acetonitrile, wherein said liquid mixture includes 2.7 grams of said ammonium azide, and wherein said liquid mixture further includes 10 milliliters of acetic acid and 100 milligrams of manganese (II) bromide tetrahydrate.

13. The method according to claim 12, further comprising stirring said liquid mixture at room temperature during said step of applying.

14. The method according to claim 8, further comprising removing said solvent from said liquid product wherein a paste is generated;
   mixing ethyl ether with said paste wherein an ethereal solution is generated that includes said constituent; and
   evaporating said ethyl ether from said ethereal solution to yield said consistent in a solid state.

15. The method according to claim 8, wherein said step of disposing includes the steps of:
   partially filling a container with said liquid mixture;
   sealing said container wherein a gaseous volume is defined in said container; and
   filling said gaseous volume with an oxygen-free gas.

16. A method of substituting an azide for hydrogen bonded to at least one tertiary carbon atom, comprising:
   providing a liquid mixture in an oxygen-free environment with a carbon electrode and a platinum electrode disposed in said liquid mixture in a spaced-apart fashion, said liquid mixture includes a solvent, ammonium azide, and a base material having said at least one tertiary carbon atom with the hydrogen bonded thereto;
   stirring said liquid mixture at room temperature;
   applying, during said step of stirring, an electric current to said carbon electrode and said platinum electrode wherein said liquid mixture undergoes a reaction to yield a liquid product and a solid product, said liquid product including said solvent and a constituent having said at least one tertiary carbon atom with an azide bonded thereto;
   removing said solvent from said liquid product wherein a paste is generated;
   mixing ethyl ether with said paste wherein an ethereal solution is generated that includes said constituent; and
   evaporating said ethyl ether from said ethereal solution to yield said constituent in a solid state.

17. The method according to claim 16, wherein said base material comprises adamantane.

18. The method according to claim 16, wherein said base material comprises adamantane, wherein said solvent comprises lithium percholate dissolved in anhydrous acetonitrile, and wherein said liquid mixture further includes acetic acid and a catalytic quantity of manganese (II) bromide tetrahydrate.

19. The method according to claim 16, wherein said base material comprises 250 milligrams of adamantane, wherein said solvent comprises 90 milliliters of 0.1 mole of lithium percholate dissolved in anhydrous acetonitrile, wherein said liquid mixture includes 2.7 grams of said ammonium azide, and wherein said liquid mixture further includes 10 milliliters of acetic acid and 100 milligrams of manganese (II) bromide tetrahydrate.

* * * * *